(12) United States Patent
McMinn

(10) Patent No.: US 6,846,329 B2
(45) Date of Patent: Jan. 25, 2005

(54) KNEE PROSTHESIS

(76) Inventor: Derek James Wallace McMinn, Calcot Farm, Calcot Hill, Clent, Stourbridge, DY9 9RX (GB)

( * ) Notice: Subject to any disclaimer, the term of this patent is extended or adjusted under 35 U.S.C. 154(b) by 0 days.

(21) Appl. No.: 10/373,436

(22) Filed: Feb. 25, 2003

(65) Prior Publication Data
US 2003/0163201 A1 Aug. 28, 2003

(30) Foreign Application Priority Data
Feb. 26, 2002 (GB) ............................................. 0204381

(51) Int. Cl.⁷ ................................................ A61F 2/38
(52) U.S. Cl. ................................ 623/20.14; 623/20.31
(58) Field of Search ........................... 623/20.14–20.36

(56) References Cited

U.S. PATENT DOCUMENTS

| | | | | |
|---|---|---|---|---|
| 3,696,446 A | * | 10/1972 | Bousquet et al. ......... | 623/20.26 |
| 3,748,662 A | * | 7/1973 | Helfet ..................... | 623/20.31 |
| 3,798,679 A | | 3/1974 | Ewald | |
| 5,116,376 A | * | 5/1992 | May ........................ | 623/20.29 |
| 5,219,362 A | * | 6/1993 | Tuke et al. .............. | 623/20.31 |
| 5,387,240 A | | 2/1995 | Pottenger et al. | |
| 5,507,820 A | * | 4/1996 | Pappas .................... | 623/20.19 |
| 5,658,342 A | | 8/1997 | Draganich et al. | |
| 5,782,925 A | | 7/1998 | Collazo et al. | |
| 6,039,764 A | | 3/2000 | Pottenger et al. | |
| 6,102,955 A | * | 8/2000 | Mendes et al. .......... | 623/20.32 |
| 6,325,828 B1 | * | 12/2001 | Dennis et al. ........... | 623/20.14 |
| 6,344,059 B1 | * | 2/2002 | Krakovits et al. ....... | 623/20.31 |
| 6,413,279 B1 | * | 7/2002 | Metzger et al. .......... | 623/20.29 |
| 6,527,807 B1 | * | 3/2003 | O'Neil et al. ............ | 623/20.15 |
| 2003/0009232 A1 | * | 1/2003 | Metzger et al. .......... | 623/20.29 |

FOREIGN PATENT DOCUMENTS

| | | |
|---|---|---|
| FR | 2 796 836 | 7/1999 |
| GB | 2223950 | 6/1992 |
| GB | 2293109 | 3/1996 |
| GB | 2313314 | 4/2000 |
| GB | 2351236 | 12/2000 |
| GB | 2323034 | 7/2001 |
| WO | 97/30663 | 8/1997 |
| WO | 01/01891 | 1/2001 |

* cited by examiner

Primary Examiner—Alvin Stewart
(74) Attorney, Agent, or Firm—Fulbright & Jaworski LLP

(57) ABSTRACT

A knee prosthesis comprises a femoral component, a tibial component and a bearing component therebetween. The femoral component defines medial and lateral condylar surfaces which are in the form of respective parts of a common helix, and the bearing component has respective surfaces matching the condylar surfaces. Accordingly a patella groove in the femoral component is laterally displaced, and on flexion of the knee, in use, from an extended position there is a lateral translatory movement of the femur. Congruent contact between the femoral component and the bearing component is maintained through at least 60° of flexion of the knee from an extended position.

9 Claims, 7 Drawing Sheets

KNEE PROSTHESIS

FIELD OF THE INVENTION

This invention relates to a knee prosthesis for fitting to a patient as a replacement knee joint.

DESCRIPTION OF THE RELATED ART

In a normal knee, the groove on the femur for the patella is laterally displaced with respect to the mid point of the femur, this lateral displacement being of the order of 5 m.m. In addition to being laterally displaced, the patella groove on the femur is laterally angulated by 7° with respect to the distal femur and knee joint.

In the normal knee therefore as it flexes, the patella articulates in the patella groove on the femur. Clearly it is thus important in knee replacement design to reproduce the natural position of the patella groove on the prosthetic femoral component. This is not presently reliably reproduced in knee replacement design, and lateral patella mal-tracking is a common cause of pain and morbidity. In one known design, part of the lateral femoral condyle prosthesis is removed to accommodate such lateral displacement of the groove. This is undesirable in producing a reduced area of contact between the lateral femoral condyle and the polyethylene articulating surface, with the potential for increased plastics wear.

In another known design the long axis of the femoral condyles is at right angles to the transverse axis of the knee joint. When the knee is extended, the patella articulates at the front of the femoral component. Since this area is not required for the tibia-femoral articulation, then metal can be removed to provide a lateral angulation to the patella groove. However when the knee is flexed, then the patella groove is the general area between the medial and lateral femoral condyles, and these condyles are involved in the tibia-femoral articulation in extension. Any attempt by a designer to angulate the patella groove will have serious detrimental effects. The more the patella groove is angulated and displaced, the more the area of articulation for the lateral femoral condyle is reduced.

SUMMARY OF THE INVENTION

The invention provides an improved knee prosthesis which reduces or obviates the disadvantages of the prior art referred to in the above section.

According to the present invention there is provided a knee prosthesis comprising a femoral component for securement to the femur, the femoral component defining medial and lateral condyles and an intercondylar groove, a tibial component for securement to the tibia, and a bearing component between the femoral and tibial components, the bearing component having respective surfaces shaped to match said condyles and engaging therewith both when the knee, in use, is extended and also over a range of flexion, the condyles being in the form of respective parts of a common helix and the respective matching surfaces of the bearing component being correspondingly part-helical.

Preferably the condyles are shaped in the manner of the threads on a screw, and the matching parts of the bearing component are shaped in the manner of threads cut in a complementary nut. However the matching parts of the bearing component could be in the manner of the threads on the screw, with the condyles shaped in the manner of the threads cut in the nut. Desirably the bearing component is a polyethylene tibal insert.

BRIEF DESCRIPTION OF THE DRAWINGS

The invention will now be described, by way of example, with reference to the accompanying drawings, in which.

DETAILED DESCRIPTION

As will be described with the knee prosthesis shown in FIGS. 5 to 12 and 24 and 25, the invention of the present application basically relates to the shaping of the medial and lateral condyles and the corresponding engagement surfaces of a tibial bearing insert, with which the condyles engage, as matching part-helical, for example in the manner of a screw-thread and associated corresponding nut engaged therewith. Although it would be possible to provide condyles in the form of the threads cut in the nut, with the threads on the screw being provided by the bearing component, it is preferred, as will be described, that the screw-threads, i.e. the male part of the thread will be defined by the condyles, with the bearing component being matchingly grooved in the nature of the threads cut in the nut. By this means, as will be more fully explained below, congruent contact can be made between the femoral component and the tibial bearing insert of the prosthesis both in the extended state of the knee and also over a range of flexion, for example up to at least 60° of bending of the knee.

Figure 1:
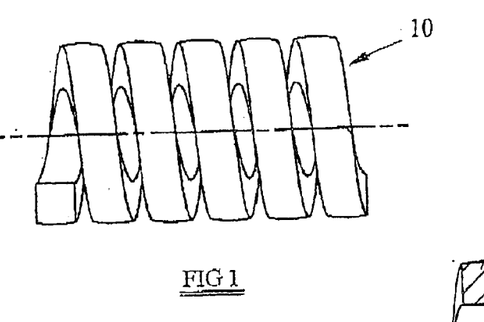
FIGS. 1 to 3 are schematic explanatory views relating to the formation of helical condyles of a femoral component of a knee prosthesis of the invention.
Figure 2:
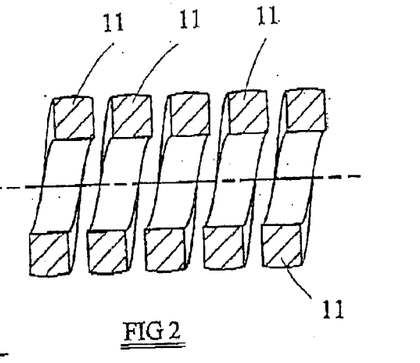
Figure 3:
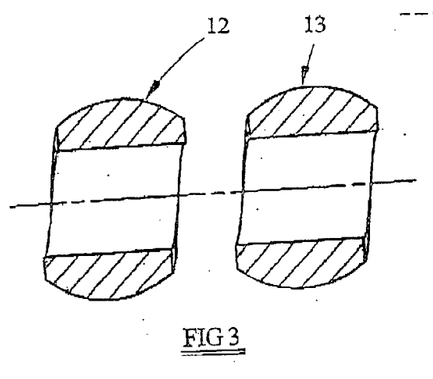

FIGS. 1 to 4 schematically show the form of the helical nature of the femoral condyles and the grooves in the tibial bearing component. FIG. 1 shows a helix 10 with a certain selected angle defining the pitch of the thread. FIG. 2 shows a section through the helix of FIG. 1 so as to define a series of spaced part-helical forms 11. It will be understood how two of these can be adapted to form the shapes of the respective sections 12, 13 shown in FIG. 3 which approximate to the condylar sections of the femoral component to be described in relation to the drawings showing the assembled prosthesis.

Figure 4:
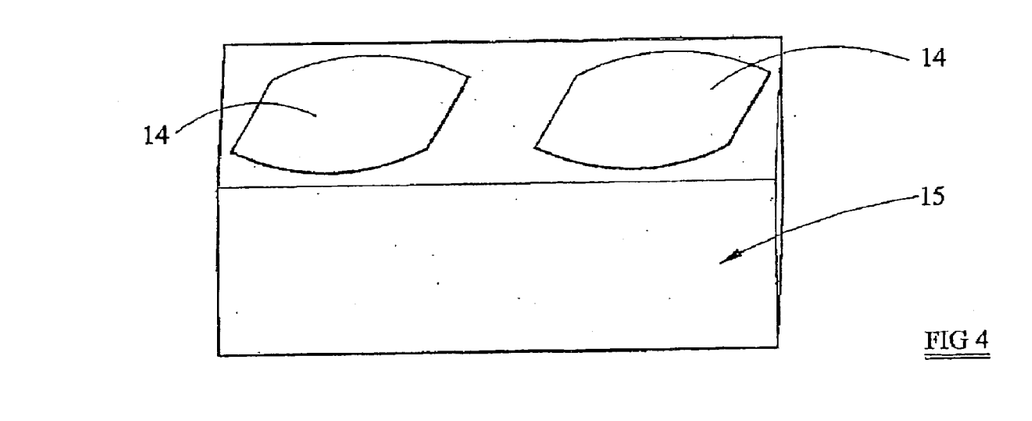
FIG. 4 is a further schematic, explanatory view showing the formation of the helical condyles and also the matching part-helical grooves of a tibial bearing insert of the knee prosthesis.

A further illustration of the nature of the part-helical arrangement of the prosthesis is shown in FIG. 4, here particularly in relation to the shapes of the respective grooves or surfaces 14 formed in the bearing component which is schematically shown in the form of a block 15. It can be seen that each groove is at an angle to the longitudinal extent of the block, this angle corresponding to the angle of the helix 16 shown in FIG. 4, with the two part-helical sections of the helix 16 corresponding respectively with the grooves 14 being equivalent to the medial and lateral condyles of the femoral component of the knee prosthesis.

FIGS. 5 to 9 show an assembled prosthesis comprising a femoral component 17, a tibial component 18, and a bearing component 19 disposed between the component 17 and 18. The bearing component, which can be considered to be a tibial insert, is preferably of plastics material to allow smooth flexing movement of the femoral component thereon, and preferably said plastics material is polyethylene. Although not essential, the prosthesis can include location means in the form of a separate stabilising peg 20. It is intended that in use the femoral component 17 is secured to the end of the femur from which bone has appropriately been removed. The component can be fixed in any suitable manner. The peg 20 is, in use, secured to the top of the tibia, again in any suitable manner, this peg extending through a central opening of the tibial component 18, as a close fit, and also extending through a central slot in the bearing component 19, in a similar manner as for the knee prosthesis in applicant's British Patent No. 2313314B. However, as mentioned, the invention is not limited to a prosthesis utilising such a peg providing a stabilised meniscus knee replacement as described and illustrated in UK Patent No. 2313314B.

Figure 10:
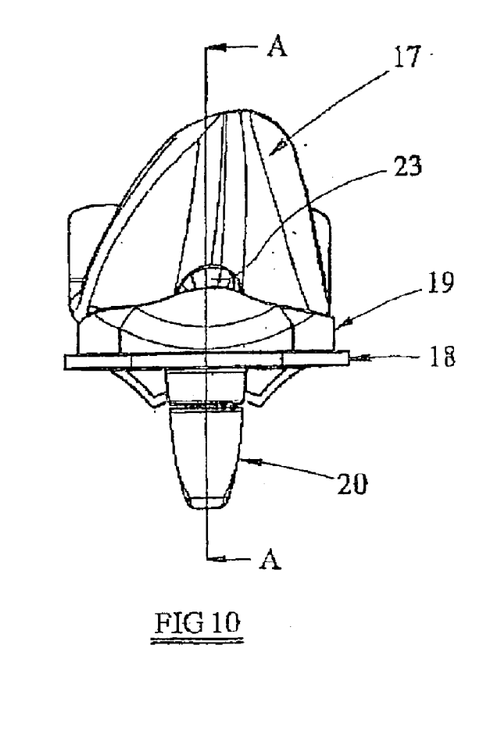
Figure 11:
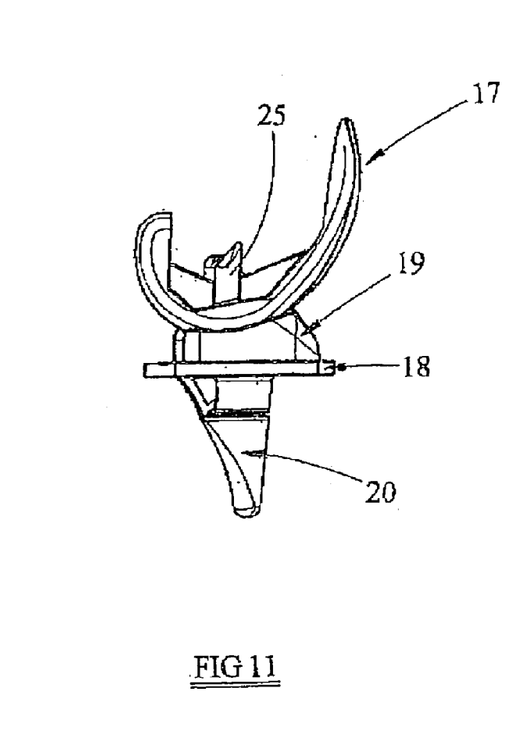
Figure 12:
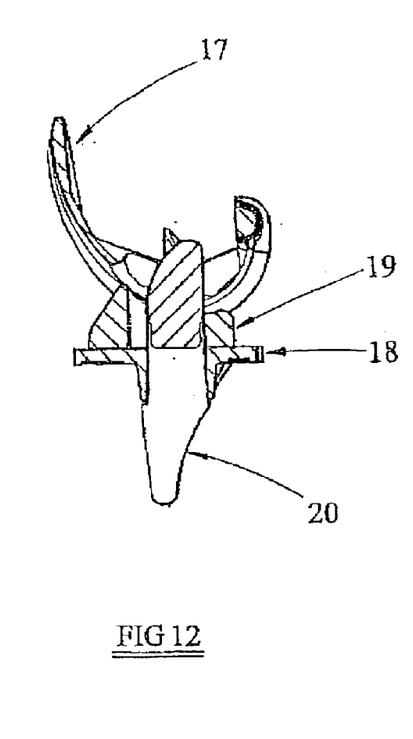

Whilst FIGS. 5 to 9 show the prosthesis in a state equivalent to one fitted to a partly flexed knee, FIGS. 10 to 12 show the state when it is fitted to a knee which is extended.

Figure 13:
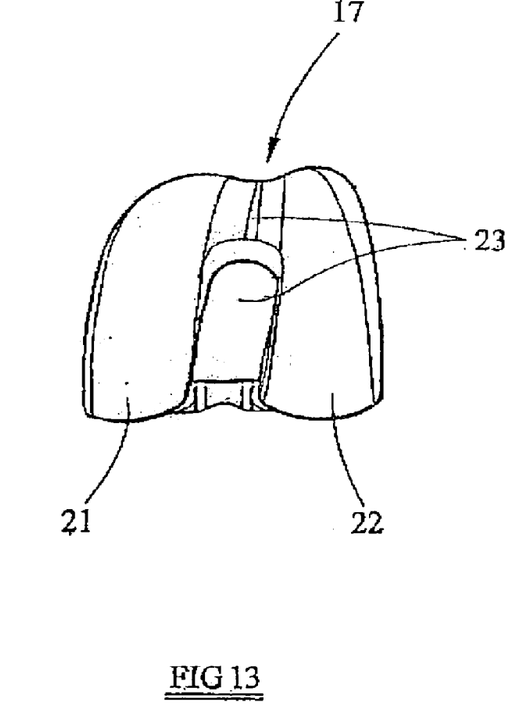
FIGS. 13 to 15 are respectively a front view, a side view and a rear view of the femoral component of the knee prosthesis.
Figure 14:
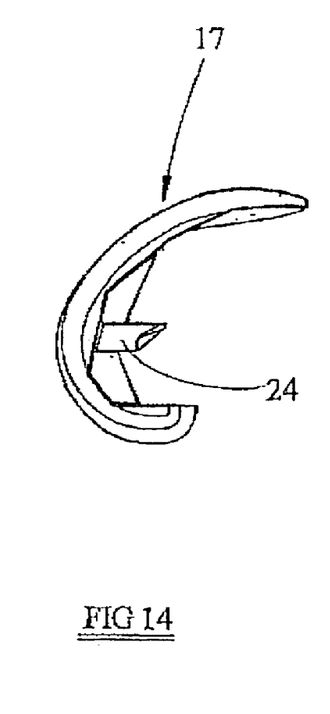
Figure 15:
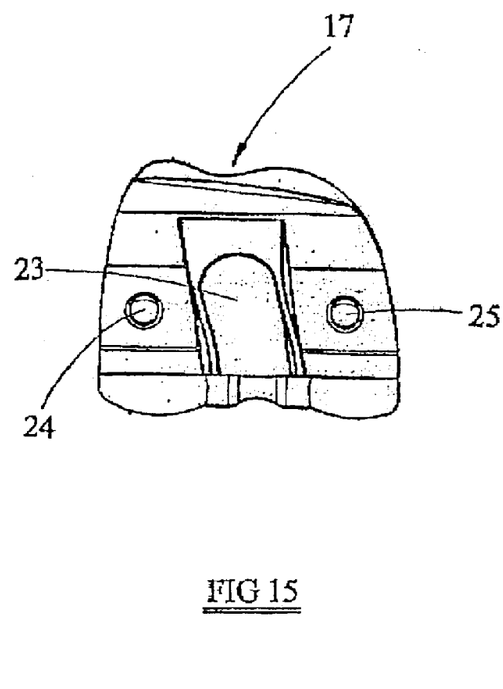

The femoral component shown in FIGS. 13 to 15 is of generally known form defining outer generally arcuate medial condylar and lateral condylar surfaces 21,22 respectively, As described above, these are shaped in the manner of screw-threads, i.e. are each part-helical, being formed from the same helix. Defined between and parallel to the medial and lateral condyles is the patella groove 23. From FIGS. 5 and 13, for example, it will be appreciated that the helical nature of the condyle results in the patellar-femoral articulation being displaced laterally with respect to the mid point of the tibial-femoral articulation. The patella groove is thus laterally displayed, the amount of lateral displacement depending upon the pitch of the 'threads' which the condyles define.

From FIGS. 14 and 15 it can be seen that at the interior surface of the femoral component 17, at respective opposite sides of the patella groove are respective pegs 24,25 to facilitate fixing of the femoral component to the end of the femur, in use.

Figure 5:
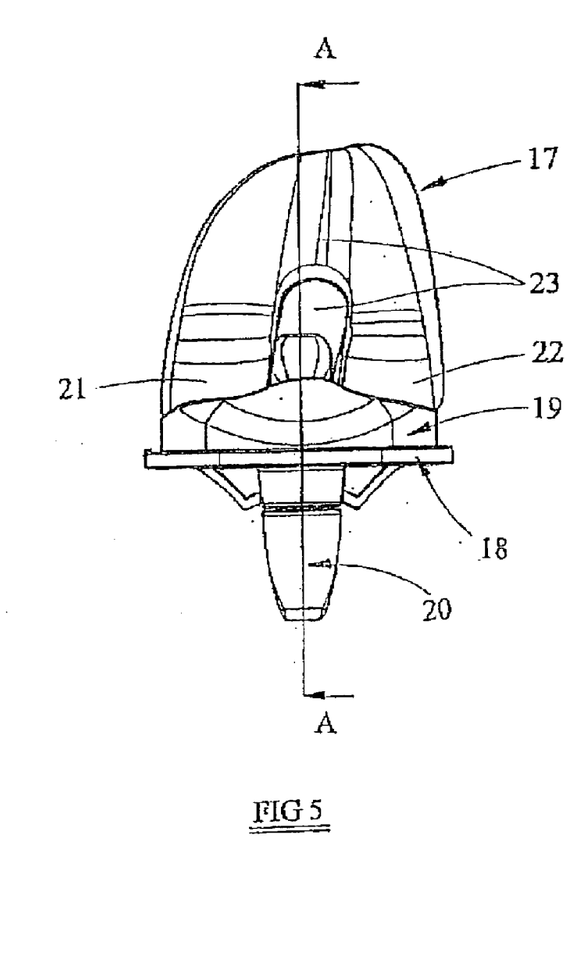
FIG. 5 is a front view of the knee prosthesis of the invention, corresponding to a partly flexed state of the knee.
Figure 6:
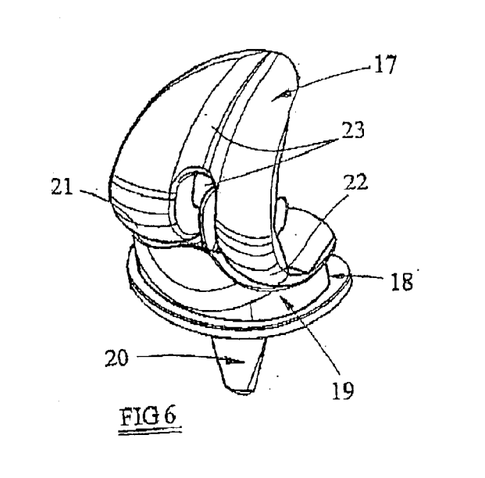
FIGS. 6 to 9 are respectively a perspective view, a view of one side, a view of the opposite side and a sectional view on line A—A of FIG. 5, of the prosthesis of FIG. 5, FIGS. 10 to 12 are views corresponding to FIGS. 5, 8 and 9 respectively, corresponding to an extended state of the knee.
Figure 7:
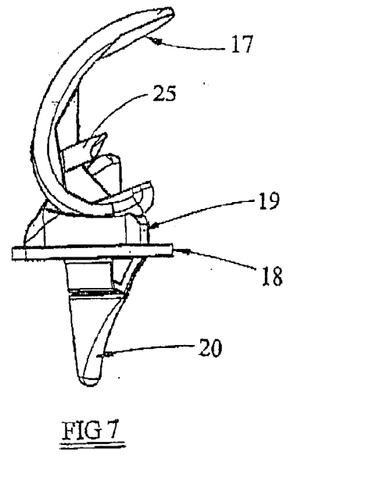
Figure 8:
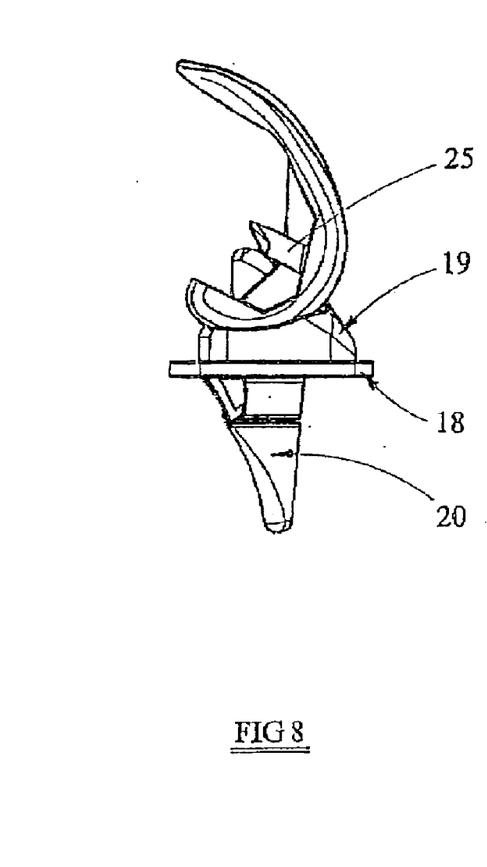
Figure 9:
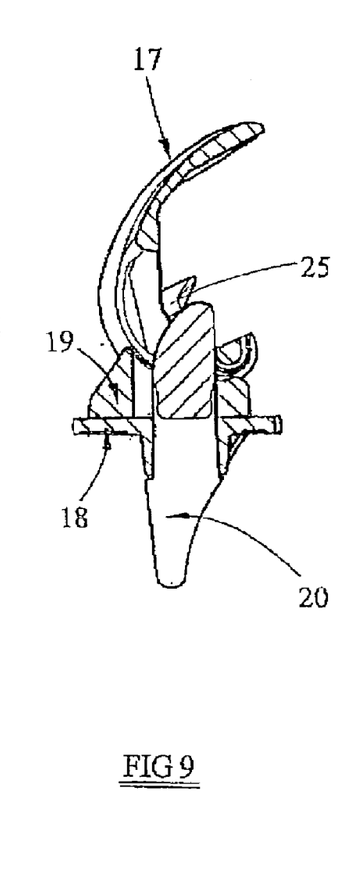
Figure 16:
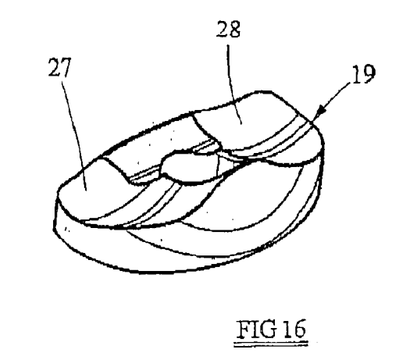
FIGS. 16 to 18 are respectively a perspective view, a plan view and a side view of a tibial bearing insert of the knee prosthesis.
Figure 17:
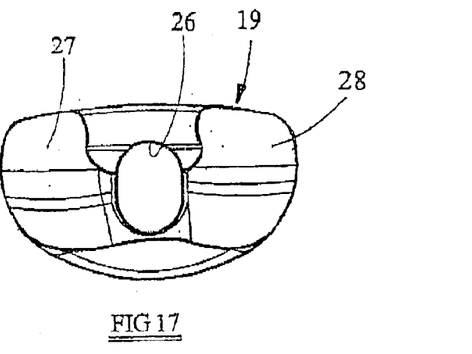
Figure 18:
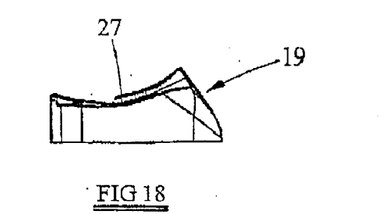
Figure 19:
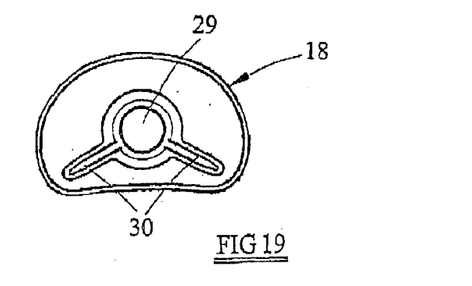
FIG. 19 is an underneath view of a tibial component of the knee prosthesis.
Figure 20:
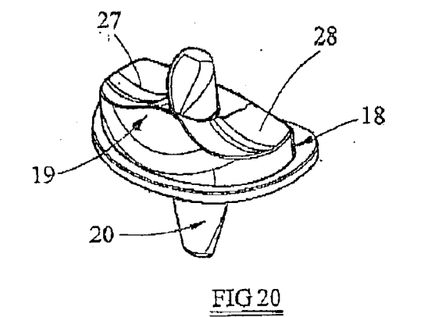
FIGS. 20 to 23 are respectively a perspective view, a front view, a plan view and a central lateral sectional view of the tibial bearing insert assembled on said tibial component, with a locating peg also being shown.
Figure 21:
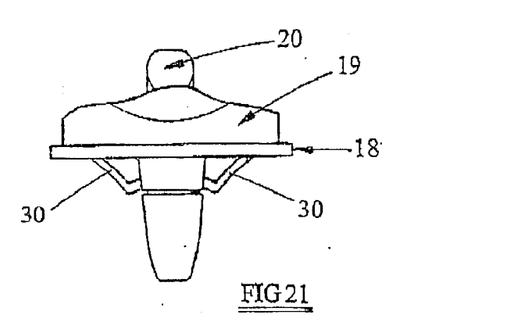
Figure 22:
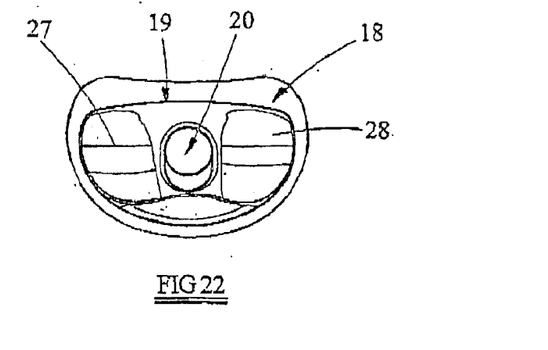
Figure 23:
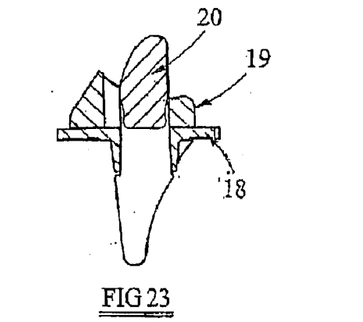

FIGS. 16 to 18 show the plastics material bearing component 19, which has said central slot 26 therein between the surfaces 27,28 respectively matching the part-helical condylar surfaces 21,22 respectively. FIG. 19 shows the tibial component 18 with a circular boss 29 at its underside so as closely to receive therethrough the peg 20, as shown, for example, in FIGS. 9 and 12. Extending from this boss are ribs 30, as also shown in FIGS. 5 and 10, to assist fixing of the tibial component 18 to the tibia, in use.

It will be appreciated that the femoral component would normally be of metallic material with its condylar surfaces highly polished. Typically it could be of cobalt chrome and would be affixed to the femur by any form of suitable cement adhesion or biological fixation. Similarly the tibial component 18 would also normally be of metallic material, again such as cobalt chrome. The peg could have its upper-portion formed of Ultra High Molecular Weight Polyethylene (UHMPE), although its lower part could be formed of cobalt chrome.

It is believed that it will be appreciated from the above, in conjunction with FIGS. 5 to 12 how the prosthesis of the invention operates, in use. As described above, the helical form of the condyles of the femoral component serves to displace the patella groove laterally. This is a static effect, with the amount of lateral displacement being proportional to the angle of the helix. Additionally the helical arrangement means that the 'helix' advances when turned relative to the bearing component. Accordingly when the knee is flexed, in use, from an extended position, the helical nature of the condyles induces a lateral translatory movement of the femoral component, and thus of the femur, upon the tibial polyethylene insert. This is a dynamic effect corresponding to the turning of a thread relative to a fixed nut. This again is desirable because the whole of the femur, and thus the patella groove also, is moved laterally with increasing flexion of the knee. However the most important aspect of this movement is that congruent contact is made between the femur and the tibial polyethylene insert throughout a significant proportion of the flexion, i.e. at least through 60° of such flexion of the knee. This is considered to be a particularly advantageous feature of the present invention in that in various proposed prior art arrangements such congruency cannot be maintained during this range of flexion.

In particular, with the arrangement illustrated, i.e. with the stabilised meniscus knee of Patent No. 2313314 incorporating the helical condyle arrangement of this application, the bearing component 19 moves rearwardly as the knee is flexed, but still remains congruent with the femoral component.

Figure 24:
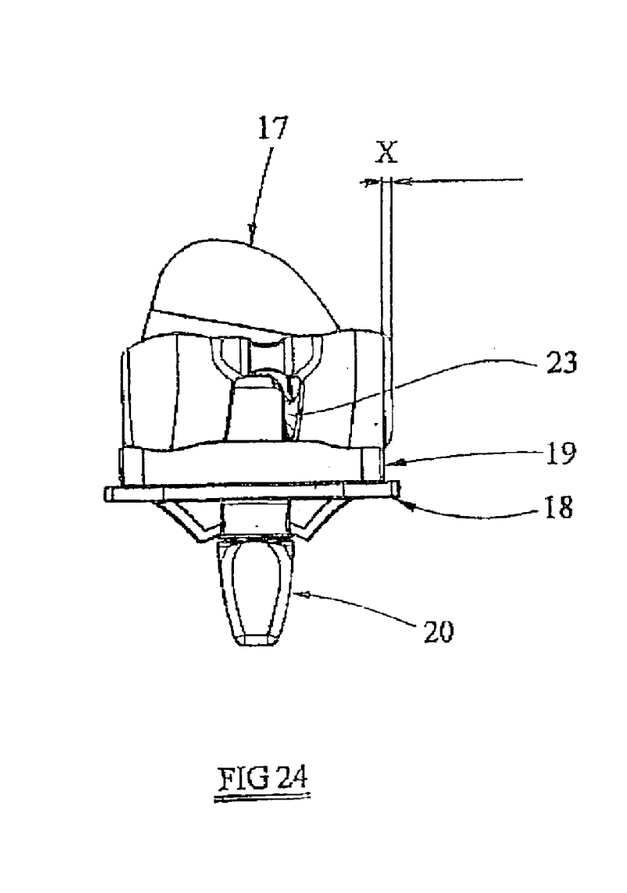
FIGS. 24 and 25 are respective rear views showing the prosthesis in fully extended and fully flexed states of the knee.
Figure 25:
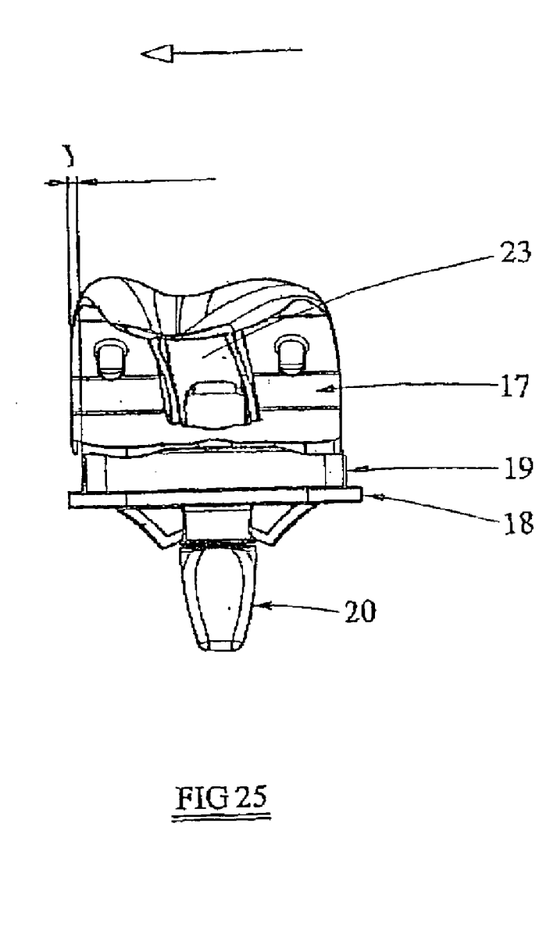

Finally FIGS. 24 and 25 show the assembled knee prosthesis in fully extended and fully flexed states of the knee, in use. Typically there is lateral translatory movement of the femur upon the tibia to the extent shown, i.e. with a lateral shift of 3.5 m.m. per 90°. These Figures show the respective overhangs X and Y at the respective opposite sides of the prosthesis in the fully extended and fully flexed states respectively.

Accordingly, in summary, the present invention enables congruent contact to be maintained between the femoral component and the bearing component throughout a range of flexion of the knee, e.g. for at least 0–60°. The helical nature of the condyles have the effect of laterally displacing the patella groove. Moreover the form of the condyles upon movement, i.e, flexing, of the knee induce a lateral translatory movement of the femur upon the tibia with increasing flexion of the knee, thus further displacing laterally the patella groove.

As a consequence of the above, it will be appreciated that this knee replacement design more faithfully reproduces the natural position of the patella groove on the prosthetic femoral component, so that desired lateral patella tracking is more faithfully achieved, thereby reducing pain and morbidity. It will also be appreciated that this required tracking is achieved without any removal of the lateral femoral condyle. Therefore there is no undesirable reduction of the area of contact between this condyle and the bearing component, and moreover, as mentioned above, congruency is maintained at this surface over a large degree of flexion.

What is claimed is:

1. A knee prosthesis comprising a femoral component for securement to the femur, the femoral component defining medial and lateral condyles and an intercondylar groove, a tibial component for securement to the tibia, and a bearing component between the femoral and tibial components, the bearing component having respective surfaces shaped to match said condyles and engaging therewith when the knee, in use, is extended and also over a range of flexion, the condyles being in the form of respective parts of a common helix and the respective matching surfaces of the bearing component being correspondingly part-helical.

2. A prosthesis as claimed in claim 1, wherein the condyles are shaped in the manner of the threads on a screw, and the matching parts of the bearing component are shaped in the manner of threads cut in a complementary nut.

3. A prosthesis as claimed in claim 1, in which a patella groove is defined between and parallel to the medial and lateral condyles, such that the patellar-femoral articulation is displaced laterally with respect to the mid point of the tibial-femoral articulation.

4. A prosthesis as claimed in claim 3, wherein the amount of lateral displacement depends upon the pitch of the helix which defines the condyles.

5. A prosthesis as claimed in claim 1, wherein flexion of the knee, in use, from an extended position induces lateral translatory movement of the femoral component upon said bearing component.

6. A prosthesis as claimed in claim 5, wherein the lateral translatory movement is 3.5 mm per 90° of flexion.

7. A prosthesis as claimed in claim 1, wherein, during flexion of the knee, in use, through at least 60° from an extended position, there is congruent contact between the femoral component and the bearing component.

8. A prosthesis as claimed in claim 1, wherein the femoral component is of metallic material, having its condylar surfaces highly polished.

9. A prosthesis as claimed in claim 1, wherein a peg, secured in use to the tibia, extends through the tibial component and through a slot in the bearing component, thereby allowing relative movement of the bearing component on flexion of the knee, in use.

* * * * *